(12) United States Patent
Coatsworth et al.

(10) Patent No.: US 11,141,563 B2
(45) Date of Patent: Oct. 12, 2021

(54) GUIDEWIRE MANAGEMENT CLIP (71) Applicant: Abbott Cardiovascular Systems Inc., Santa Clara, CA (US)

(72) Inventors: Lauren Coatsworth, Murrieta, CA (US); Jimmy L. Quijas, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 17/177,121

(22) Filed: Feb. 16, 2021

(65) Prior Publication Data

US 2021/0187239 A1 Jun. 24, 2021

Related U.S. Application Data

(62) Division of application No. 16/530,843, filed on Aug. 2, 2019, now Pat. No. 11,033,711.

(51) Int. Cl.
*A61M 25/00* (2006.01)
*A61M 25/09* (2006.01)
*A61B 90/94* (2016.01)
*A61B 50/20* (2016.01)
*B25B 11/00* (2006.01)

(52) U.S. Cl.
CPC .......... *A61M 25/002* (2013.01); *A61B 50/20* (2016.02); *A61B 90/94* (2016.02); *A61M 25/09* (2013.01); *B25B 11/00* (2013.01); *A61M 2025/09116* (2013.01); *A61M 2207/00* (2013.01); *A61M 2209/08* (2013.01)

(58) Field of Classification Search
CPC ............. A61B 50/20; A61B 90/90–96; A61M 25/002; A61M 2025/0177; A61M 25/02; A61M 2025/024; A61M 25/09041; A61M 2209/06; A61M 2209/08; A61M 2205/6063–6081; A61M 2207/00; B25B 11/00
See application file for complete search history.

(56) References Cited

U.S. PATENT DOCUMENTS

| 3,636,595 A | 1/1972 | Wines |
| 3,696,920 A * | 10/1972 | Lahay ................... A61B 50/30 206/370 |
| 1,860,757 A | 8/1989 | Lynch et al. |
| 5,027,478 A | 7/1991 | Suhr |
| 5,125,906 A | 6/1992 | Fleck |
| 5,263,671 A | 11/1993 | Baum |

(Continued)

*Primary Examiner* — Matthew P Travers
(74) *Attorney, Agent, or Firm* — Fulwider Patton LLP (57) ABSTRACT

A method for managing a guidewire in preparation for a surgical operation, comprising attaching a block of resilient polymer to a coiled tube which contains a guidewire; attaching to the block of resilient polymer a card having printed information concerning the guidewire on a planar surface of the card; removing the guidewire from the coiled tube; removing the block of resilient polymer from the coiled tube while keeping the card having printed information attached to the block of resilient polymer; coiling the guidewire into a flat spiral form; capturing, in a slot formed in the block of resilient polymer, a plurality of portions of the guidewire, which portions are adjacent to and parallel with each other, thereby maintaining the guidewire in the flat spiral form.

5 Claims, 7 Drawing Sheets

(56) References Cited

U.S. PATENT DOCUMENTS

| | | | |
|---|---|---|---|
| 5,344,011 A | 9/1994 | DiBernardo et al. | |
| 5,366,444 A | 11/1994 | Martin | |
| 5,730,150 A | 3/1998 | Peppel et al. | |
| 5,827,202 A | 10/1998 | Miraki et al. | |
| D406,749 S | 3/1999 | Selk | |
| 6,405,414 B1 | 6/2002 | Byrnes et al. | |
| D459,977 S | 7/2002 | Byrnes et al. | |
| 7,461,741 B2 | 12/2008 | State et al. | |
| D622,132 S | 8/2010 | DeMars et al. | |
| 7,886,906 B1 | 2/2011 | Dunn | |
| D676,314 S | 2/2013 | Cude | |
| D775,937 S | 1/2017 | Davis | |
| D841,802 S | 2/2019 | Wakabayashi et al. | |
| 2004/0073233 A1 | 4/2004 | Jannot | |
| 2005/0277888 A1* | 12/2005 | Propp | A61M 25/02 604/174 |
| 2006/0237597 A1* | 10/2006 | D'Andria | F16L 3/223 248/68.1 |
| 2010/0006738 A1 | 1/2010 | Teirstein | |
| 2010/0010475 A1 | 1/2010 | Teirstein et al. | |
| 2016/0073862 A1* | 3/2016 | Matsuno | A61B 50/33 606/47 |
| 2016/0074628 A1 | 3/2016 | Smith et al. | |
| 2017/0281901 A1* | 10/2017 | Otake | A61M 25/002 |
| 2018/0207416 A1* | 7/2018 | Roddy | A61M 25/02 |
| 2018/0304049 A1 | 10/2018 | Bennett et al. | |

\* cited by examiner

GUIDEWIRE MANAGEMENT CLIP

CROSS-REFERENCES TO RELATED APPLICATIONS

This application is a divisional application based on U.S. Ser. No. 16/530,843, filed Aug. 2, 2019, incorporated by reference in its entirety.

BACKGROUND

The present invention relates to guidewires used in anatomical surgery. More specifically, the invention relates to systems and methods for managing and identifying guidewires once they have been removed from safe storage during preparation for use on a patient.

Guidewires are an essential component of modern minimally invasive surgery. Guidewires are extremely thin, but stiff, metal wires that are configured to be inserted into a patient's vasculature at a convenient point such as the femoral artery in the leg, or the radial artery in the arm, and to be advanced through the patient's vasculature until the distal tip reaches a desired part of the patient's anatomy. Once the guidewire is in the correct position in relation to the vasculature, a catheter carrying a further functional device such as a balloon or a stent may be advanced over the guidewire and deployed, and then the catheter may be withdrawn. In many cases, a second catheter with a different functional device may be advanced over the same guidewire. Thus, the guidewire may play the role of an "anchor" in a pathway into the anatomy. The difficult task of tracking the guidewire up through the anatomy need be performed only once, where after the guidewire is kept in position to assist with the performance of a number of procedures. After all procedures are accomplished, the guidewire may finally be withdrawn.

Typically, a guidewire is sold by its manufacturer in a protective plastic tube that is formed into a flat spiral, suitable for insertion into a box for shipment. As the procedure advances, and the patient is made ready, the guidewire may be removed from its storage/delivery tube. At this moment, the guidewire is extremely awkward to handle, because it is about 6 feet to 9 feet long, and may whip around and come into contact with unsanitized equipment or even the floor. If any delaying event intervenes before introducing the guidewire into the patient, then the surgeon has his or her hands full because the guidewire must be controlled, while the delaying event must be eliminated. This may require extra preparation of the patient by the surgeon, who will be obliged to put down the guidewire to free up his or her hands for the task. Even if this can be managed, a further problem may arise when the surgeon is ready to proceed. Frequently it may occur that a second guidewire or even a third guidewire having entirely different characteristics has been removed from its tube in anticipation of its use, due to an intervening problem that becomes apparent. The surgeon then has the task of physically controlling two or three guidewires, and also of distinguishing between them. Guidewires are notoriously difficult to distinguish one from another because they are so thin, and include little structure in addition to the tubular wire itself by which to make an identification.

There is therefore a need in the art for a method, device, and system to enable a surgeon to keep physical control of a guidewire removed from its original container, and to identify and distinguish those that have been removed from others that are similarly removed. The present invention addresses these and other problems in the art.

SUMMARY OF THE INVENTION

In some embodiments, the invention is a guidewire management system comprising a block of resilient polymer having a top surface, a bottom surface, a front surface, a back surface, a left surface and a right surface. A first slot is shaped to extend between the back surface and the front surface, and from the top surface towards the bottom surface without passing through the bottom surface. A second slot is shaped to extend between the back surface and the front surface, and from the top surface towards the bottom surface without passing through the bottom surface. A third slot shaped to extend between the back surface and the front surface, and from the top surface towards the bottom surface without passing through the bottom surface. A fourth slot shaped to extend between the back surface and the front surface, and from the top surface towards the bottom surface without passing through the bottom surface. The fourth slot has a first width adjacent the top surface, and wherein the first width of the fourth slot becomes narrower as the fourth slot extends towards the bottom surface such that, at a certain point, the fourth slot has a second width narrower than the first width, and further wherein, as the fourth slot extends downward beyond the certain point towards the bottom surface, the fourth slot has a third width greater than the second width; a card having a planar surface for receiving printed information, the card including an opening adjacent an edge of the card, the opening being sized to receive a portion of the block of resilient polymer, whereby the card is held in a fixed position in relation to the block of resilient polymer.

In some embodiments, the fourth slot is shaped to be formed only from curves that join each other tangentially. In further embodiments, the first width is not less than 0.02 inches. In yet further embodiments, the second width is not more than 0.010 inches. In other embodiments, the third width is not less than 0.04 inches. In further embodiments, the first slot includes a horizontal slit extending through a vertical wall of the first slot.

In another aspect, the invention is a method for managing a guidewire in preparation for a surgical operation. The method comprises attaching a block of resilient polymer to a coiled tube which contains a guidewire, then attaching to the block of resilient polymer a card having printed information concerning the guidewire on a planar surface of the card. The guidewire is removed from the coiled tube. The block of resilient polymer is removed from the coiled tube while keeping the card having printed information attached to the block of resilient polymer. The guidewire is coiled into a flat spiral form. In a slot formed in the block of resilient polymer, a plurality of portions of the guidewire are captured, which portions are adjacent to and parallel with each other, thereby maintaining the guidewire in the flat spiral form.

In some embodiments, attaching a block of resilient polymer to a coiled tube includes distorting the block of resilient polymer to alter its shape from its normal shape in order to attach it between coils of the coiled tube, and, in further comprising, allowing the block of resilient polymer to resume its normal shape when attached to the coiled tube. In some embodiments, attaching to the block of resilient polymer a card having printed information includes inserting a portion of the block of resilient polymer through an opening in the card.

In some embodiments, capturing portions of the guidewire in a slot of the block of resilient polymer includes deforming a portion of the block of resilient polymer to open a slot wide enough to insert the portions of guidewire, and in some embodiments, further comprising capturing portions of the guidewire in a space in the slot which is large enough to allow the block of resilient polymer to assume its normal shape despite the presence of the portions of the guidewire in the space.

In some embodiments, the method further comprises, preventing the sections of the guidewire from escaping from the space without further deforming the block of resilient polymer.

In some embodiments, capturing a plurality of portions of the guidewire includes capturing three, four, or five portions of the guidewire.

DETAILED DESCRIPTION OF THE PREFERRED EMBODIMENTS

In a preferred embodiment, the invention is a clip 10, and an associated method, for managing and identifying a guidewire. Specifically, the clip is for managing a guidewire that has been removed from its original flat spiral storage tube. The clip is made of a resilient rubber or synthetic polymer, allowing for some resilient movement of the parts of the clip in relation to each other during use. In a preferred embodiment, the polymer may be Santoprene® which is a dynamically vulcanized alloy consisting mostly of fully cured rubber particles encapsulated in a polypropylene matrix, available from Exxon Mobil Corporation.

The structure of the clip is set forth here.

In a preferred embodiment, the clip 10 generally occupies the space of a three dimensional block having a substantially rectangular shape, and having a front side 12, a back side 14, a right side 16, a left side 18, a bottom side 20, and a top side 22. Preferably, the dimensions of the clip may be about 1 inch extending from left side to right side, about 0.30 inches from top side to bottom side, and about 0.30 inches from front side to back side.

Various slots are formed in the clip to facilitate the functional purpose of the clip. In a preferred embodiment, three tube slots 24, 26, 28 are formed, each with an opening in the top side 22, and the slots extend between the front side 12 and the back side 14. At least each of two of the tube slots includes a cylindrical portion having a radius R1 sized to snugly receive a length of a known flat spiral storage tube 100 (FIG. 7) inside of which a guidewire 102 of known structure may be stored. In preferred embodiments, this dimension R1 may be 0.075 inches, which gives a diameter of about 0.15 inches. Each of the tube slots has a narrowed neck opening having a dimension Φ1 of about 0.075 inches. The purpose of the neck is to facilitate attachment of the clip to a coiled tube for storing the guidewire.

Figures 4A, 4B:
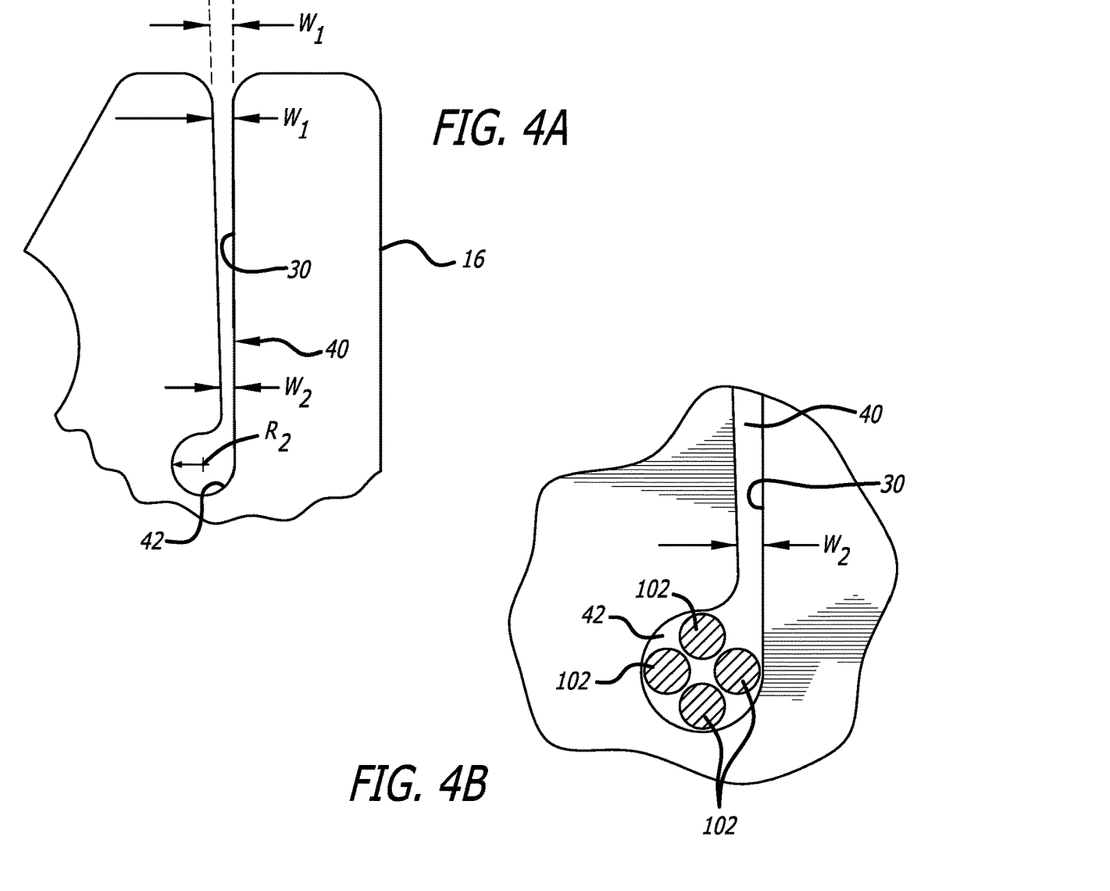
FIG. 4A is a detail view of a portion of the clip of FIG. 1, identified in FIG. 1 by the circle marked 4A.
FIG. 4B is a detail view of the portion of the clip shown in FIG. 4A, shown with guidewire portions in section.
Figure 8:
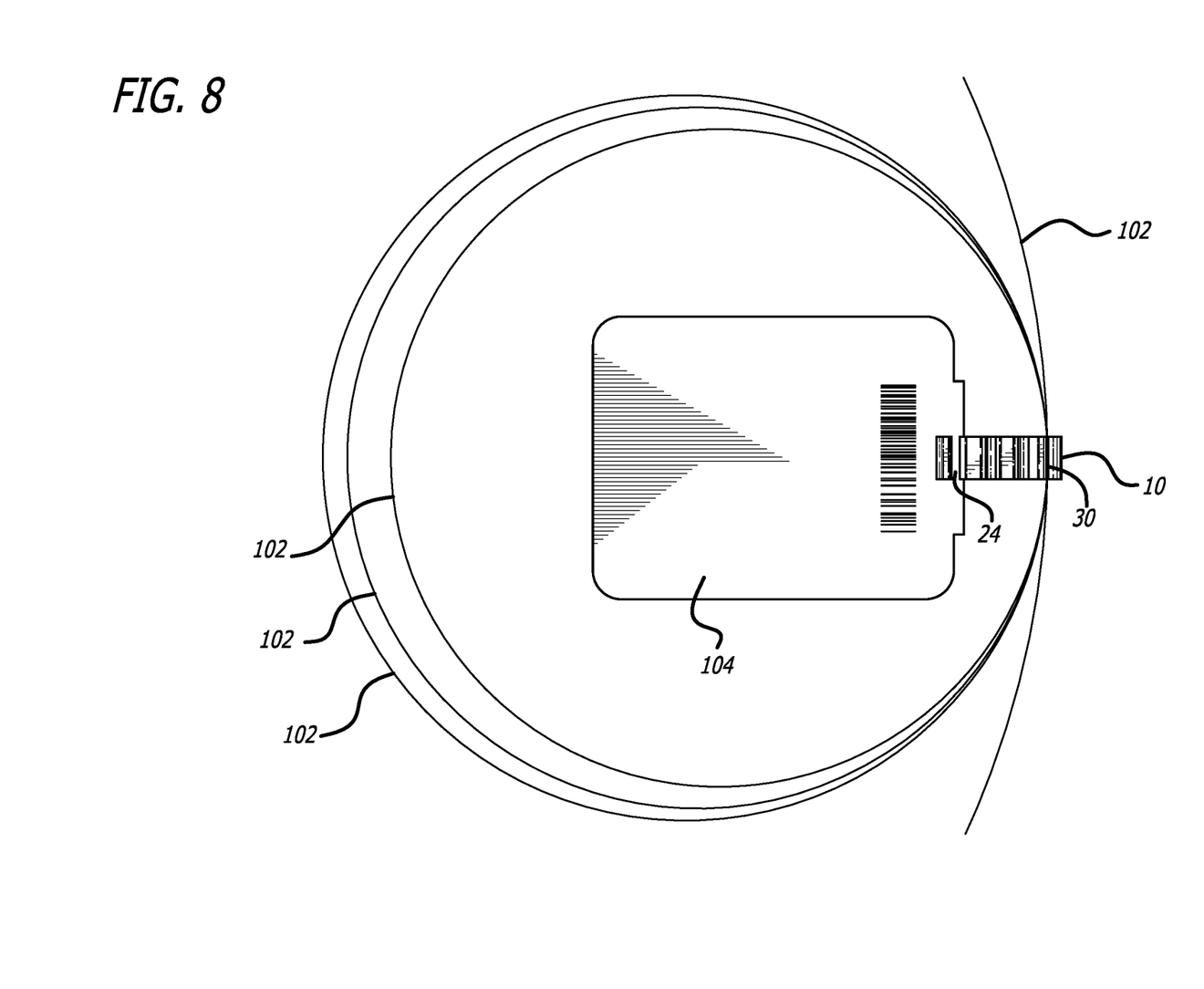
FIG. 8 is a top plan view of the clip shown in FIG. 1, shown in conjunction with a known coiled guidewire.

In the presently described embodiment, a fourth slot being a management slot 30 is formed in the clip 10 with an opening in the top side 22. The management slot extends between the front side 12 and the back side 14 of the clip 10. At its base, which is closest portion of the management slot to the bottom side 20, the management slot 30 has a cylindrical "capture zone" 42 having a radius R2, which is sized to comfortably receive a plurality of looped portions of a guidewire 102. (FIG. 4B and FIG. 8.) A typical guidewire is between about 0.014 inches and 0.018 inches in diameter, so that radius R2 is preferably about 0.02 inches in dimension, which gives a diameter of about 0.04 inches. This diameter will permit about three to five loops of a typical guidewire to be stored in the capture zone 42 without distorting the capture zone from its normal shape.

The usefulness of the clip is set forth here.

Figure 5:
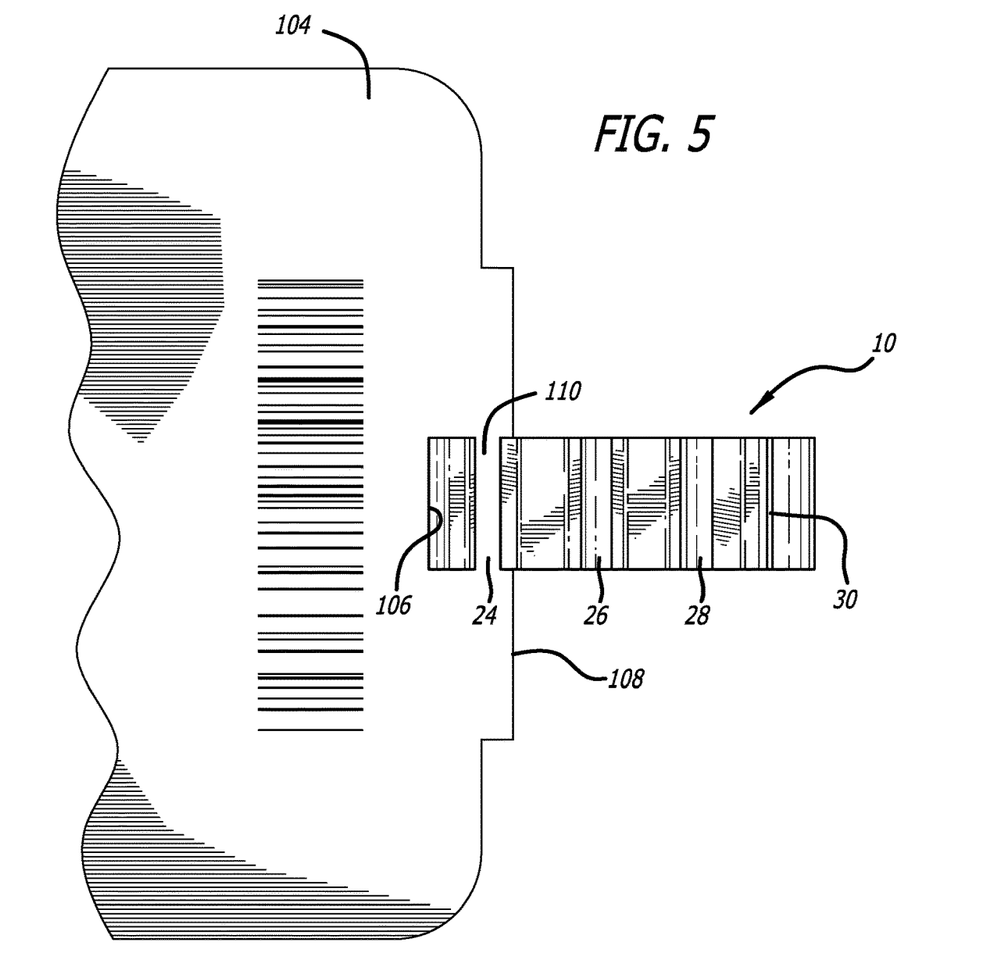
FIG. 5 is a top plan view of the clip of FIG. 1, to which a label has been attached.
Figure 6:
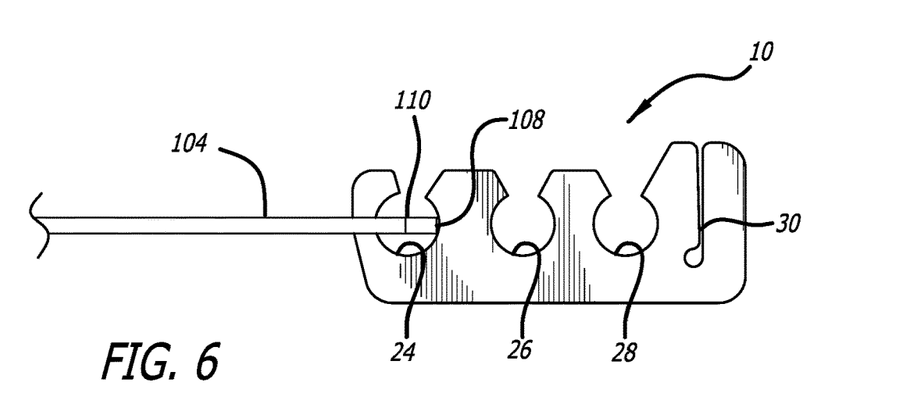
FIG. 6 is a side elevational view of an embodiment the clip shown in FIG. 1 together with a label as shown in FIG. 5.

The features of the clip 10 thus described allow the clip 10 to be advantageously used as follows: In a first stage of its use, a label 104 with printed matter identifying the guidewire may be attached to the clip 10 as seen in FIG. 5 and FIG. 6. The label is initially formed with an opening 106 in the label, parallel with an edge 108 of the label, so that a narrow band 110 is formed with a width that matches (i.e., is slightly larger than, to allow a tight fit) the diameter (twice R1) of the first slot 24. This band 110 is then inserted into the slot 24 where it is held securely so that the label may be read by the user.

Figure 7:
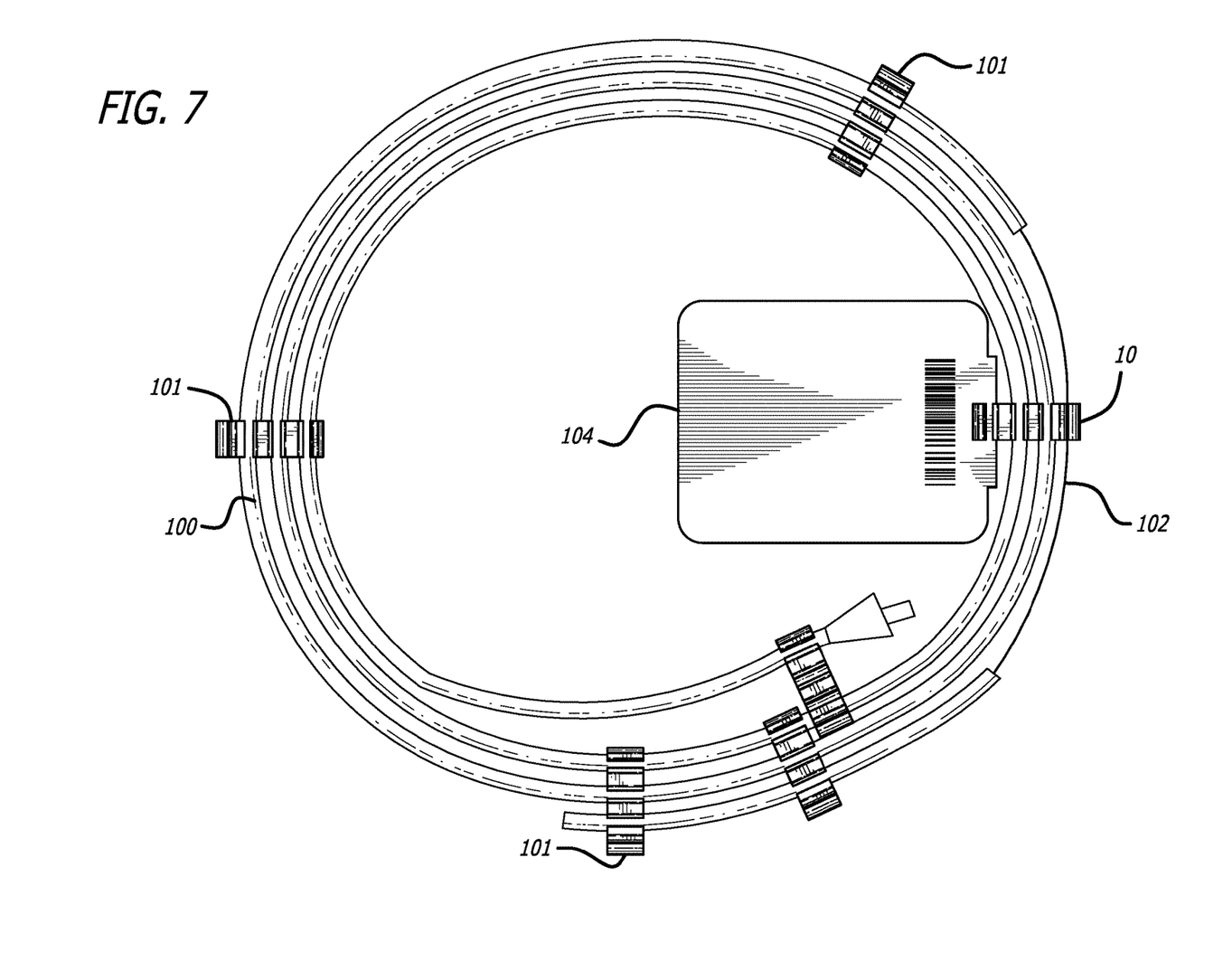
FIG. 7 is a plan view of the clip shown in FIG. 1, in conjunction with a known coiled tube for storing a known guidewire.

The clip 10 is, in turn, installed on a flat spiral tube 100 which has been manufactured in known fashion to store and transport the guidewire 102. (FIG. 7.) While the spiral tube may be held in its own flat spiral condition with known clips 101 of suitable structure, the clip 10 of the invention may be installed on top of the coils by inserting the coils into the slots 26 and 28, as seen in FIG. 6 and FIG. 7. The first slot 24 may be reserved for attaching the label as described above.

Figure 1:
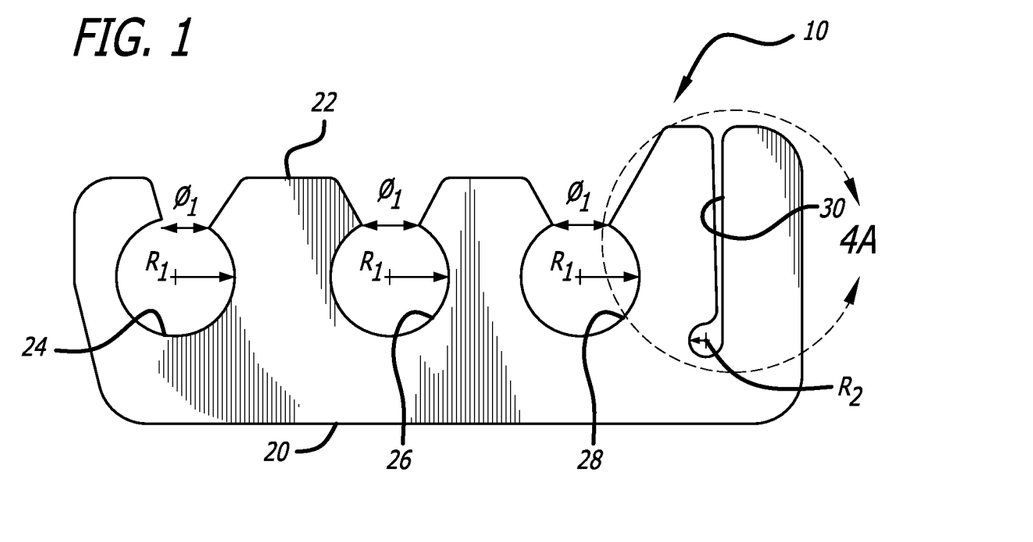
FIG. 1 is a side elevational view of an embodiment of the clip having features of the invention.
Figure 1A:
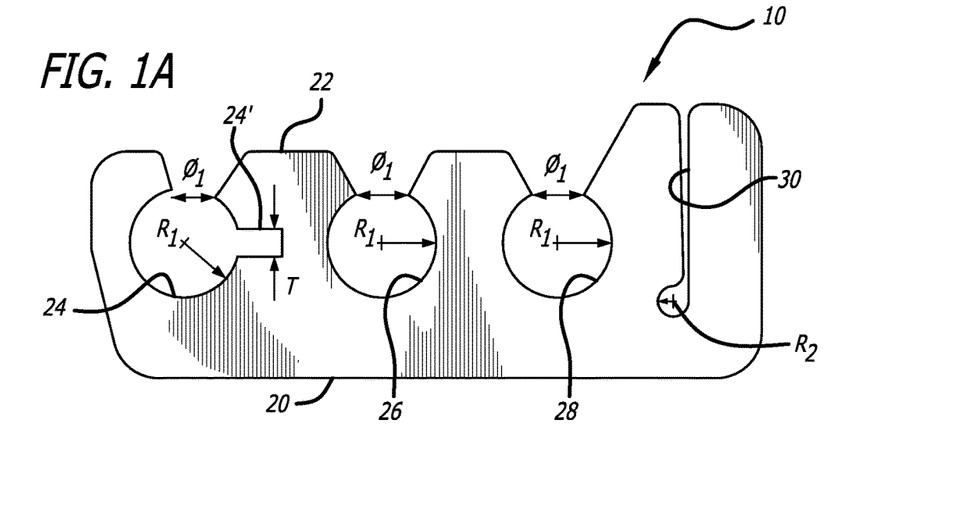
FIG. 1A is a side elevational view of another embodiment of the clip having features of the invention.
Figure 2:
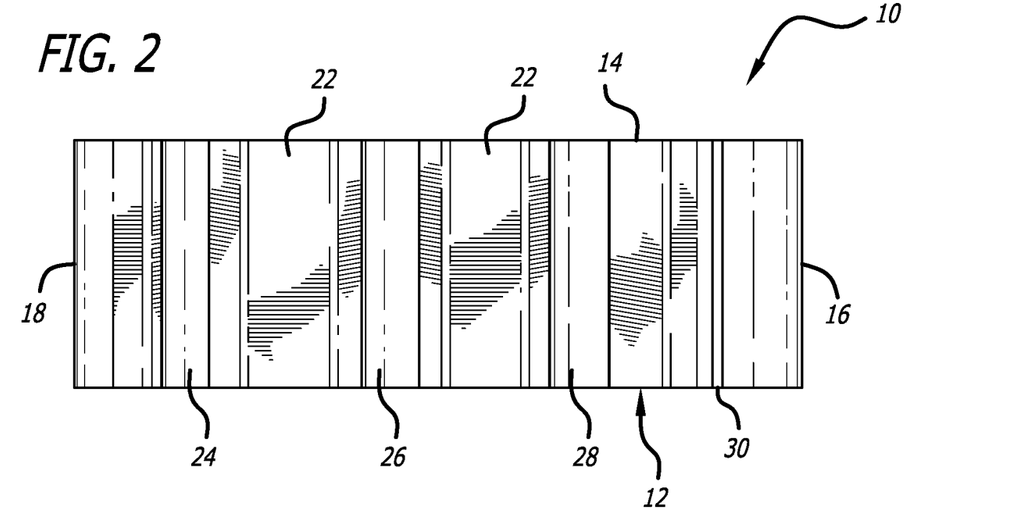
FIG. 2 is a top plan view of the clip of FIG. 1.
Figure 3:
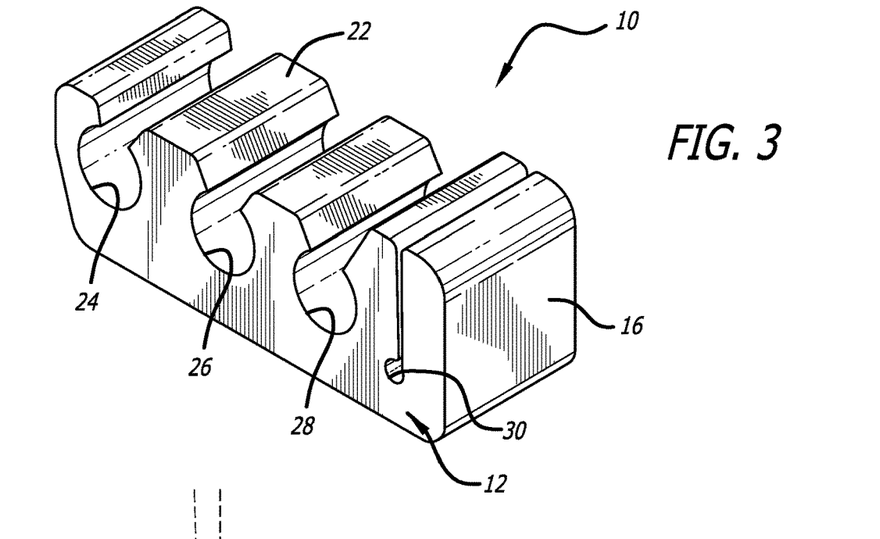
FIG. 3 is a perspective view of the clip of FIG. 1.
Figure 3A:
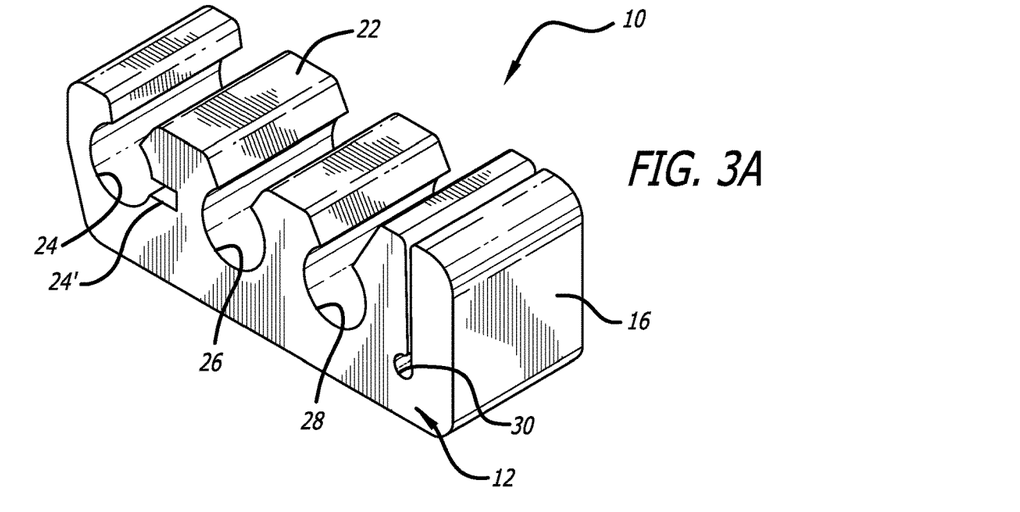
FIG. 3A is a perspective view of an embodiment of the clip shown in FIG. 1A.
Figure 6A:
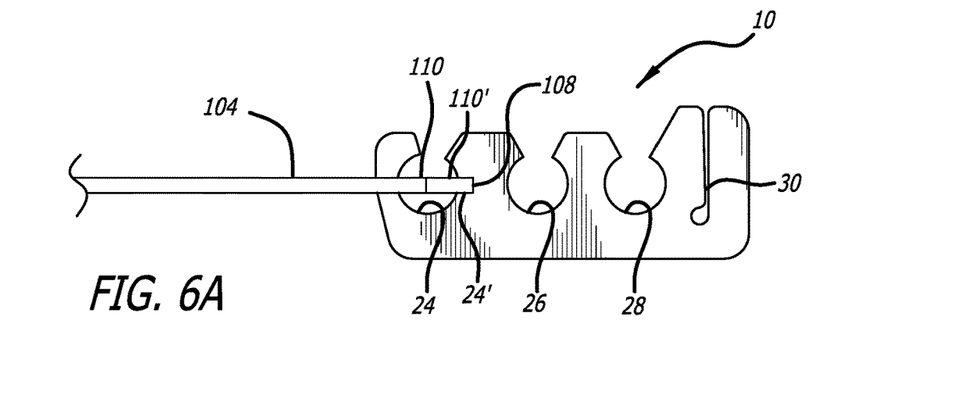
FIG. 6A is a side elevational view of an embodiment of the clip shown in FIG. 1A, together with a label.

In another embodiment a variation of the slot 24 is shown in FIG. 1A, FIG. 3A and FIG. 6A. In this embodiment, the slot 24 is modified to include, in a vertically extending wall of the slot 24, a horizontally extending slit 24' having a rectangular profile with a vertical thickness "T" (see FIG. 1A) sufficient to easily receive the thickness of the label 104. This slit 24' permits the band 110 of the label to be made slightly wider, so that a portion of the band 110 occupies the slit 24' on one side of the band, and the label is thus provided with an enhanced resistance against rotation in the slot 24.

Figure 4C:
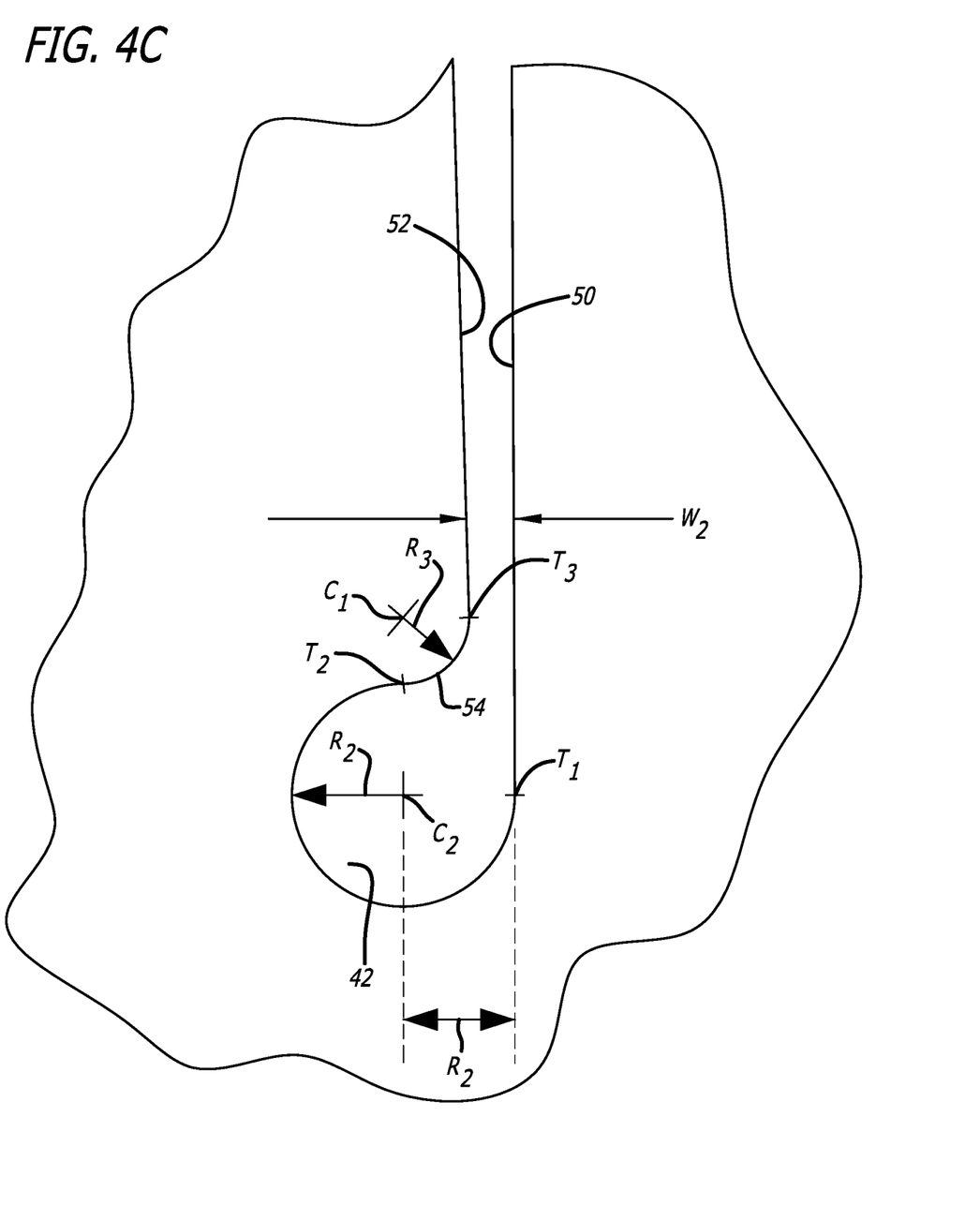
FIG. 4C is a detail view of the portion of the clip shown in FIG. 4B, in greater detail.

In a second stage in the use of the clip, the shape of the management slot 30 may be envisaged by reference to FIG. 4A, FIG. 4B and FIG. 4C. As will be described in detail below, the shape of the management slot allows the physician user of the clip to coil up a guidewire 102 after it has been removed from its storage tube 100, and capture all the windings of the guidewire inside the management slot 30 so that the coils do not tend to spring out and escape from their capture location. This advantageous outcome is exemplified in FIG. 4B and FIG. 8.

In the condition shown in FIG. 8, the clip 10 performs two advantageous functions:

First, the clip provides an anchor for supporting the label 104. The label 104 is attached to the clip (FIG. 5, FIG. 6 and FIG. 7) while the guidewire is within the storage tube 100 (FIG. 7), and the clip is attached to the storage tube. In this condition, the physician can identify the characteristics of the guidewire while it is in the storage tube. Then, subsequently, as explained below, when the clip is attached to the guidewire 102 by inserting coil portions of the guidewire into the management slot 30 (FIG. 8) the physician can identify the characteristics of the guidewire 102 after removal from the storage tube 100.

Second, the clip 10 and the shape of the management slot 30 allows the physician user of the clip to coil up a guidewire 102 after it has been removed from its storage tube 100, and capture all the windings of the guidewire inside the management slot 30 (FIG. 4B and FIG. 8) such that the coils do not tend to spring out and escape from their capture location. Thus, the physician may place the guidewire to one side in this well managed condition, confident that it will not escape from the confines of the clip 10, and where the physician may at a glance identify the characteristics of the guidewire from the printed matter on the label 104. The physician may, at his own convenience, easily remove the guidewire from the management slot, and proceed to use the guidewire in the performance of the operation in the appropriate sequence.

As a result of the features of the clip 10 described herein, the physician user has at his or her disposal a system and method for solving the problem previously described above that confronts the art, in which a physician begins preparing to insert a guidewire into the vasculature of a patient, but, before he can do so, he is distracted by some other procedure requiring a different guidewire having different characteristics that must be completed first. This may require that he place the first guidewire, having been removed from the storage tube, in a location near the patient, and prepare a second guidewire for an intermediate purpose. In some instances, the physician user may return to using the first guidewire, but because two guidewires are now removed from their storage tubes, the physician may be confused as to which one is which. In addition to being confused as to which guidewire is which, the additional problem may arise that the two guidewires, extending about 6 feet to 9 feet, are effectively uncontrollable, whipping around and defying the physician to gain control of both ends at once. Thus, the advantages of the clip 10 of the present invention may be fully appreciated because both the problem of identification and of management are addressed.

A further structural aspect of the design is set forth here.

In order to conveniently accomplish the purpose of the invention, the management slot 30 may be shaped to have a neck portion 40 which, adjacent the exit of the neck portion through the upper surface 22 has a width "W1" of not less than about 0.02 inches when the clip 10 is in a normal condition. ("Normal condition" is used herein to mean when the clip is in an unloaded condition without any structures such as the spiral tube 100 or guidewire portions 102 impinging upon it or in it.) The rationale behind the size of W1 is that it should be at least wide enough to easily permit the physician user to slide a portion of the bare guidewire into the management slot at the top surface 22. In light of the fact that the average diameter of a guidewire is between about 0.014 inches and 0.018 inches, the size of W1 at 0.02 inches permits the guidewire portion to be introduced without initially requiring distortion of the clip 10 at the point of entry into the management slot 30.

Seen from the front face of the clip, the neck portion 40 empties out at a lower end into a cylindrical portion, or capture zone 42. The capture zone 42 is formed to be large enough to contain a plurality of portions (preferably 3 to 5) of a single guidewire 102 that has been looped around in a tight spiral after being removed from the spiral storage tube 100. (See FIG. 4A, FIG. 4B and FIG. 8.) A feature of the capture zone 42 of the management slot 30 is that it is shaped to have an opening into the neck portion 40 which has a dimension "W2" which is about 0.010 inches. In light of the fact that the average diameter of a guidewire is between about 0.014 inches and 0.018 inches, the width of "W2" at 0.010 inches means that sliding a portion of guidewire down the management slot into the capture zone 42 must distort the polymer comprising the clip 10, so that once the guidewire portion has entered the capture zone 42, the guidewire portion will be compelled to distort the clip in order to exit the capture zone. This feature provides an advantageous level of security, in that it "captures" any portion of guidewire that is inserted into the capture zone 42, and tends to hold that portion within its space. Only by distorting the shape of the clip can the coiled guidewire be removed. Thus, the physician user must remove the bare guidewire from the capture zone 42 by distorting the resilient clip 10 to widen the opening into the neck portion beyond its "normal" size. This configuration provides an advantageous aspect that maintains the guidewire portions 102 within the capture zone 42, from where they do not tend to fall out when acted on merely by gravitational force, but where they require a distortion of the clip provided by the physician to force them out.

Another aspect of the cylindrical capture zone 42 of the management slot is that it may connect into the neck portion 40 of the management slot 30 via an opening that is specially shaped to facilitate introducing and removing the portions of the guidewire 102 to and from the capture zone 42. The neck portion 40 of the management slot is formed by two almost (but not exactly) parallel sides, a right side 50, and a left side 52. See, FIG. 4C. The capture zone 42 may be formed by a cylinder that includes three fourths of a circular cylinder. The inner surface of the right side 50 joins the inner surface of the capture zone 40 at a tangential transition point T1. The inner surface of the left side 52 joins the inner surface of the capture zone 42 via a transition curve 54 formed by a radial inner surface as described here: A portion of a circular curve 54 having radius R3 makes tangential contact, at a tangential transition point T2, with the inner portion of the curvature of the capture zone. Whereas the inner surface of the capture zone 42 has a positive curvature, the inner surface of the transition curve 54 has a negative curvature. At an end of the transition curve 54 that is opposite the transition point T2, the inner surface of the transition curve 54 tangentially joins the inner surface of the left side 52 of the neck at transition point T3. Thus, all points of transition from one uniform curvature surface to an adjacent curvature are tangentially transitioned. Yet, at the same time, the narrow neck 40 emptying into the capture zone 42 will prevent the captured guidewire portions from simply falling out of the capture zone.

This feature provides a smooth tactile experience for the user physician when inserting portions of guidewire 102 into the capture zone 42 or when removing it. This is an advantageous result for the following reasons: When the physician is ready to use the coiled guidewire and acts to remove the guidewire portions from the capture zone, the described configuration of the curved portions provide a tactile response such that what he feels does not include any "sticking" point, in which the guidewire portions come up against a sharp corner or a corner that includes a sudden change of slope. Such a sticking point is undesirable because it may cause the physician to hesitate in order to check whether in fact the guidewire is free to be removed, or whether it is stuck and will need unexpected force to remove it.

Another advantageous feature of the opening from the capture zone 42 into the neck 40 of the clip is that the center C1 of the circular transition curve 54 is positioned vertically above the center C2 of the circular capture zone. This means that the line drawn through center C1 and center C2 is parallel to the linear surface formed by the left side 52. Finally, the dimension for R3 is chosen so that the tangential requirements are satisfied with the distance W2 being about 0.010 inches, and the radius R2 of the capture zone being about 0.02 inches given an overall diameter or width of 0.04 inches. These geometric features allow the physician to conveniently remove the coiled guidewire by initially forcing the captured portions laterally against the right wall 50 of the management slot, followed by a vertical force that takes them out of the management slot in a single straight line movement without encountering any changes in direction.

Accordingly, there is described a novel system and method that addresses needs and shortcomings in the art. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A guidewire management system comprising:
   a block of resilient polymer having a top surface, a bottom surface, a front surface, a back surface, a left surface and a right surface;
   a first slot shaped to extend between the back surface and the front surface, and from the top surface towards the bottom surface without passing through the bottom surface, wherein the first slot includes a horizontal slit extending through a vertical wall of the first slot;
   a second slot shaped to extend between the back surface and the front surface, and from the top surface towards the bottom surface without passing through the bottom surface;
   a third slot shaped to extend between the back surface and the front surface, and from the top surface towards the bottom surface without passing through the bottom surface;
   a fourth slot shaped to extend between the back surface and the front surface, and from the top surface towards the bottom surface without passing through the bottom surface,
   wherein
   the fourth slot has a first width adjacent the top surface, and wherein the fourth slot becomes narrower as the fourth slot extends towards the bottom surface such that, at a certain point, the fourth slot has a second width narrower than the first width, and further wherein, as the fourth slot extends downward beyond the certain point towards the bottom surface, the fourth slot has a third width greater than the second width; and
   a card having a planar surface for receiving printed information, the card including an opening defining a band adjacent an edge of the card, the opening receiving a portion of the block of resilient polymer, and the card is held in a fixed position in relation to the block of resilient polymer by a portion of the band occupying the horizontal slit.

2. The guidewire management system of claim 1, wherein the fourth slot is shaped to be formed only from curves that join each other tangentially.

3. The guidewire management system of claim 1, wherein the first width is not less than 0.02 inches.

4. The guidewire management system of claim 1, wherein the second width is not more than 0.010 inches.

5. The guidewire management system of claim 1, wherein the third width is not less than 0.04 inches.

* * * * *